(12) United States Patent
Horz et al.

(10) Patent No.: US 8,929,632 B2
(45) Date of Patent: Jan. 6, 2015

(54) TEMPORAL DIFFERENCE ENCODING FOR ANGIOGRAPHIC IMAGE SEQUENCES

(71) Applicants: Tim Horz, Nürnberg (DE); Markus Kowarschik, Langenzenn (DE)

(72) Inventors: Tim Horz, Nürnberg (DE); Markus Kowarschik, Langenzenn (DE)

(73) Assignee: Siemens Aktiengesellschaft, Munich (DE)

( * ) Notice: Subject to any disclaimer, the term of this patent is extended or adjusted under 35 U.S.C. 154(b) by 217 days.

(21) Appl. No.: 13/621,889

(22) Filed: Sep. 18, 2012

(65) Prior Publication Data

US 2013/0077839 A1  Mar. 28, 2013

Related U.S. Application Data

(60) Provisional application No. 61/537,836, filed on Sep. 22, 2011.

(51) Int. Cl.
*G06T 5/00* (2006.01)
*A61B 6/00* (2006.01)
*G06T 11/00* (2006.01)

(52) U.S. Cl.
CPC ............... *A61B 6/481* (2013.01); *A61B 6/504* (2013.01); *A61B 6/5211* (2013.01); *G06T 11/001* (2013.01)
USPC .......................................... 382/130; 382/162

(58) Field of Classification Search
CPC ... G06T 7/0012; G06T 7/2053; G06T 11/001; G06T 2207/30101; G06T 2207/30104; G06K 2209/05; G06K 2209/051; A61B 6/481; A61B 6/504; A61B 6/5211

USPC .............. 382/128, 130, 132, 162; 348/32, 34; 378/62, 98.12
See application file for complete search history.

(56) References Cited

U.S. PATENT DOCUMENTS

| 2004/0096088 A1* | 5/2004 | Kohle .......................... 382/128 |
| 2012/0136243 A1* | 5/2012 | Boese et al. ................. 600/425 |
| 2014/0100451 A1* | 4/2014 | Tolkowsky et al. .... A61B 6/504 |

OTHER PUBLICATIONS

C.J. Lin, S.C. Hung, W.Y. Guo, F.C. Chang, C.B. Luo, J. Beilner, M. Kowarschik, W.F. Chu, and C.Y. Chang, "Monitoring Peri-Therapeutic Cerebral Circulation Time: A Feasibility Study Using Color-Coded Quantitative DSA in Patients with Steno-Occlusive Arterial Disease", American Journal of Neuroradiology, Epub Apr. 2012, 6 pages.
C.M. Strother, F. Bender, Y. Deuerling-Zheng, K. Royalty, K.A. Pulfer, J. Baumgart, M. Zellerhoff, B. Aagaard-Kienitz, D.B. Niemann, and M.L. Lindstrom, "Parametric Color Coding of Digital Subtraction Angiography", American Journal of Neuroradiology, May 2010, pp. 919-924, vol. 31, No. 5.

* cited by examiner

*Primary Examiner* — Andrew W Johns

(57) ABSTRACT

A method of visualizing changes in blood flow in a digital subtraction angiography (DSA) image sequence is disclosed. A time-contrast curve is generated for all pixels in each image of the DSA image sequence. A reference parameter for each time-contrast curve to be used as a first time point is specified. The value of the reference parameter for each time-contrast curve is determined and an arbitrary parameter is specified for each time-contrast curve to be used as a second time point. An output image is generated by applying a color-coding of the difference between the first time point and the second time point to all pixels.

19 Claims, 9 Drawing Sheets

TEMPORAL DIFFERENCE ENCODING FOR ANGIOGRAPHIC IMAGE SEQUENCES

CROSS-REFERENCE TO RELATED APPLICATIONS

This application claims the benefit of Provisional U.S. Patent Application Ser. No. 61/537,836, entitled, "Temporal Difference Encoding for Angiographic Image Sequences", filed in the name of Tim Horz and Markus Kowarschik, on Sep. 22, 2011, the disclosure of which is hereby incorporated herein by reference.

FIELD OF THE INVENTION

This invention generally relates to medical X-ray imaging and, more particularly, to visualizing temporal data for digital subtraction angiography (DSA) and other angiographic data.

BACKGROUND OF THE INVENTION

Today, minimally invasive intravascular therapies are routinely performed in catheterization laboratories to treat numerous diseases. These diseases include strokes, vessel malformations, stenoses and tumors. Minimally invasive intravascular therapies are typically performed under image guidance in order to give the physician or health professional valuable real-time feedback, for example, visualization and localization of catheters and other tools/objects relative to the anatomy of interest of a patient. Various imaging systems and techniques may be used to provide this image guidance. For example, during these interventions, angiographic imaging systems may acquire data such as fluoroscopy sequences, 3D datasets (C-arm CT imaging), and 2D DSA image sequences.

DSA is an imaging method in which radiographic images of blood vessels are produced by subtracting a pre-contrast image (i.e., the "mask image") from later images after a contrast agent has been administered to the patient. Background anatomical structures such as bones and soft tissue are removed, leaving the blood vessels clearly visualized and highly contrasted against a neutral background. DSA has long been a preferred technique for visualizing blood vessels in medical procedures, when appropriate.

Using image post-processing algorithms and techniques, DSA sequences may also provide significant quantitative data concerning changes in blood flow and, consequently, an evaluation of a respective intravascular therapy. For example, time-density (or time-contrast) curve analysis can track changes of contrast agent density as a function of time in the DSA sequences. Generally, time-contrast curves are obtained or generated from a DSA image sequence by selecting a same region of interest in the DSA input images (also referred to as "frames") and measuring the average contrast density value within the region for each frame of the DSA sequence corresponding to a particular time (t). The area-average contrast density values are then plotted as a function of time. FIG. 1 shows a typical time-contrast curve. The start of the curve corresponds to the contrast inflow to the region of interest, with the upward curve slope indicating the rate of contrast inflow. The peak of the curve directly correlates to the amount of contrast agent in the region of interest. The back of the curve relates to the time the contrast remains in the region of interest.

Recently introduced, the syngo iFlow software product enables users a novel view of DSA data by condensing all the information inside a complete DSA sequence into one single color image using advanced color coding techniques. In essence, every pixel of the single, generated image encodes time information describing the passing-through of the contrast agent, e.g. at the time point of maximal opacification, i.e., the "time-to-peak opacification" (which is the information actually being encoded in the current version of the iFlow product). Alternatively, every pixel could contain information about the time point of the highest slope of the corresponding time-contrast curve, or any other temporal parameter determined from the DSA sequence and color encoded accordingly. This color-coding approach is described further in an article by C. J. Lin, S. C. Hung, W. Y. Guo, F. C. Chang, C. B. Luo, J. Beilner, M. Kowarschik, W. F. Chu, and C. Y. Chang, entitled "Monitoring Peri-Therapeutic Cerebral Circulation Time: A Feasibility Study Using Color-Coded Quantitative DSA in Patients with Steno-Occlusive Arterial Disease", American Journal of Neuroradiology, Epub April 2012, 6 pages, and color-coding of DSA sequences is more generally described in an article by C. M. Strother, F. Bender, Y. Deuerling-Zheng, K. Royalty, K. A. Pulfer, J. Baumgart, M. Zellerhoff, B. Aagaard-Kienitz, D. B. Niemann, and M. L. Lindstrom, entitled "Parametric Color Coding of Digital Subtraction Angiography", American Journal of Neuroradiology, May 2010, pp. 919-924, Vol. 31, No. 5, each of the above references being hereby incorporated by reference herein.

The following outlines the existing color coding approach. The input image data for the syngo iFlow algorithm is a time series of 2D acquisitions, where every pixel in each input image/frame of the DSA image sequence represents a path measurement of the object's x-ray attenuation along the x-ray from the x-ray source to the corresponding detector pixel. For each image pixel, this allows for the calculation of $I_{max}$ (representing the maximum of the amount of contrast agent along the respective x-ray) and $T_{max}$ (representing the time point of the maximum opacification due to contrast agent) as follows:

$$I_{max}(x, y) = \max_{t_a \leq t \leq t_b} [I(t_{mask}, x, y) - I(t, x, y)] \text{ and}$$

$$T_{max}(x, y) = \max\_at_{t_a \leq t \leq t_b} [I(t_{mask}, x, y) - I(t, x, y)],$$

where the image sequence is defined as I(t, x, y); the time point that defines the mask image is $t_{mask}$; and the start and end time points for the iFlow image are defined as $t_a$ and $t_b$, respectively. Note that the mask image in DSA imaging is needed for subtraction purposes in order to get rid of all anatomical background.

As a last step, the syngo iFlow algorithm uses color coding to fit the information into a single pixel. For each image pixel, the $T_{max}$ value is encoded by assigning a pure red color value to t=0 (a user-specified starting time point), a pure blue color value to a user-specified end time point, a pure green color value to the half-time of this interval and linearly interpolating the value between the three colors. The $I_{max}$ value is normalized to [0 . . . 1] (i.e., all the $I_{max}$ values lay in the range 0 to 1) and used as the opacity for the pixel. Thus, the time of the maximum opacification of each pixel becomes associated with a color and the various colors represent the early, middle and late flow in the section of the DSA sequence being viewed. The colors do not relate necessarily to the typical phases of contrast flow. The result is a single "composite time" image showing the history of the contrast agent flow. FIG. 3 illustrates this color look-up, i.e., the iFlow color encoding for one pixel, with reference to a time-contrast curve. FIG. 3 shows the single, resulting image after applying the color look-up for each pixel of FIG. 2 (which shows a red through blue spectrum bar along the time axis, the marked $T_{max}$ being in the light green scale). In FIG. 3, the brightest blood vessels (mainly in the image center, from bottom to middle) are color-coded in red, orange or yellow, the medium bright blood vessels (the smaller vessels throughout the image but mainly surrounding the center) are color coded in light green, green, blue-green or light blue, and the darkest blood vessels (along the left and bottom left periphery of the image) are color coded blue or dark blue.

Improvements to this existing color coding method are possible. Since the existing method visualizes all the temporal information inside one color image, it requires the user to visually scan this image thoroughly for the information they need. Details can therefore be overlooked easily. Also, contrary to the static nature of the iFlow images, the human visual system is optimized for detecting motion. A static image does not take advantage of this and a visualization method that allows for animating the information of iFlow images could enhance the existing method.

SUMMARY OF THE INVENTION

An embodiment of the invention obviates the above problems by providing a method of visualizing changes in blood flow in a digital subtraction angiography (DSA) image sequence, comprising generating a time-contrast curve for all pixels in each image of the DSA image sequence; specifying a reference parameter for each time-contrast curve to be used as a first time point; determining the value of the reference parameter for each time-contrast curve; specifying an arbitrary parameter for each time-contrast curve to be used as a second time point; and producing an output image by applying a color-coding of the difference between the first time point and the second time point to all pixels. The reference parameter may comprise a fixed reference time point. The fixed reference time point may comprise a pixel-specific temporal parameter determined from the DSA image sequence. Alternatively, the fixed reference time point may comprise a time-to-peak opacification time point. The arbitrary parameter may comprise a global time parameter that is not pixel-specific. Also, the difference between the first time point and the second time may be a positive value or a negative value.

The method may further comprise producing at least one additional output image by changing the value of the arbitrary parameter by a fixed or variable amount; applying a color-coding of the difference between the first time point and the changed second time point to all pixels; and producing a dynamic series of output images. Alternatively, the method may further comprise producing an animation of output images by repeating the specifying an arbitrary parameter and producing steps to obtain a plurality of output images for dynamic display.

An embodiment of the invention may also provide a method of visualizing temporal data for digital subtraction angiography (DSA) and other angiographic data of an image, comprising obtaining a time-contrast curve for all pixels in the image; specifying a first time point and a second time point for each time-contrast curve; and producing an output image that encodes the time differences between the first and second time points. One of the first and second time points may comprise a fixed reference time point. The first fixed reference time point may comprise a pixel-specific parameter of the time-contrast curve. One of the first and second time points may also comprise an arbitrarily-selected time point. The arbitrarily-selected time point may comprise a global non-pixel-specific parameter of the time-contrast curve. The producing step may comprise producing an output image that color-encodes the time differences between the first and second time points in the image. The time differences may have either positive difference values or negative difference values.

The method may further comprise dynamically changing one of the first and second time points such that an animated representation of the DSA and other angiographic data of the image results. Alternatively, the method may further comprise varying one of the first and second time points to obtain a sequence of temporal difference encoding images and producing a dynamic image sequence.

An embodiment of the invention may also provide a method of visualization of an image sequence, comprising per-pixel encoding of information relative to a reference time point for the image sequence, said information being the amount of time passed between the reference time point and an arbitrarily-selected time point and producing an encoded image. The per-pixel encoding may comprise per-pixel color-encoding using an arbitrary color mapping.

An embodiment of the invention may also provide a system for visualizing temporal data for angiographic images, comprising an imager that acquires image data of an anatomical region of a patient and a processor that manipulates the image data to produce a single image which is color-encoded for the time difference between two selected time points of a time-contrast curve for each respective pixel of the image data. The processor may manipulate the image data to produce a dynamic series of images, each of which is color-encoded for the time difference between two respective selected time points of a time-contrast curve for each respective pixel of the image data.

BRIEF DESCRIPTION OF THE DRAWINGS

For a better understanding of the present invention, reference is made to the following description of exemplary embodiments thereof, and to the accompanying drawings, wherein.

DETAILED DESCRIPTION

Figure 1:
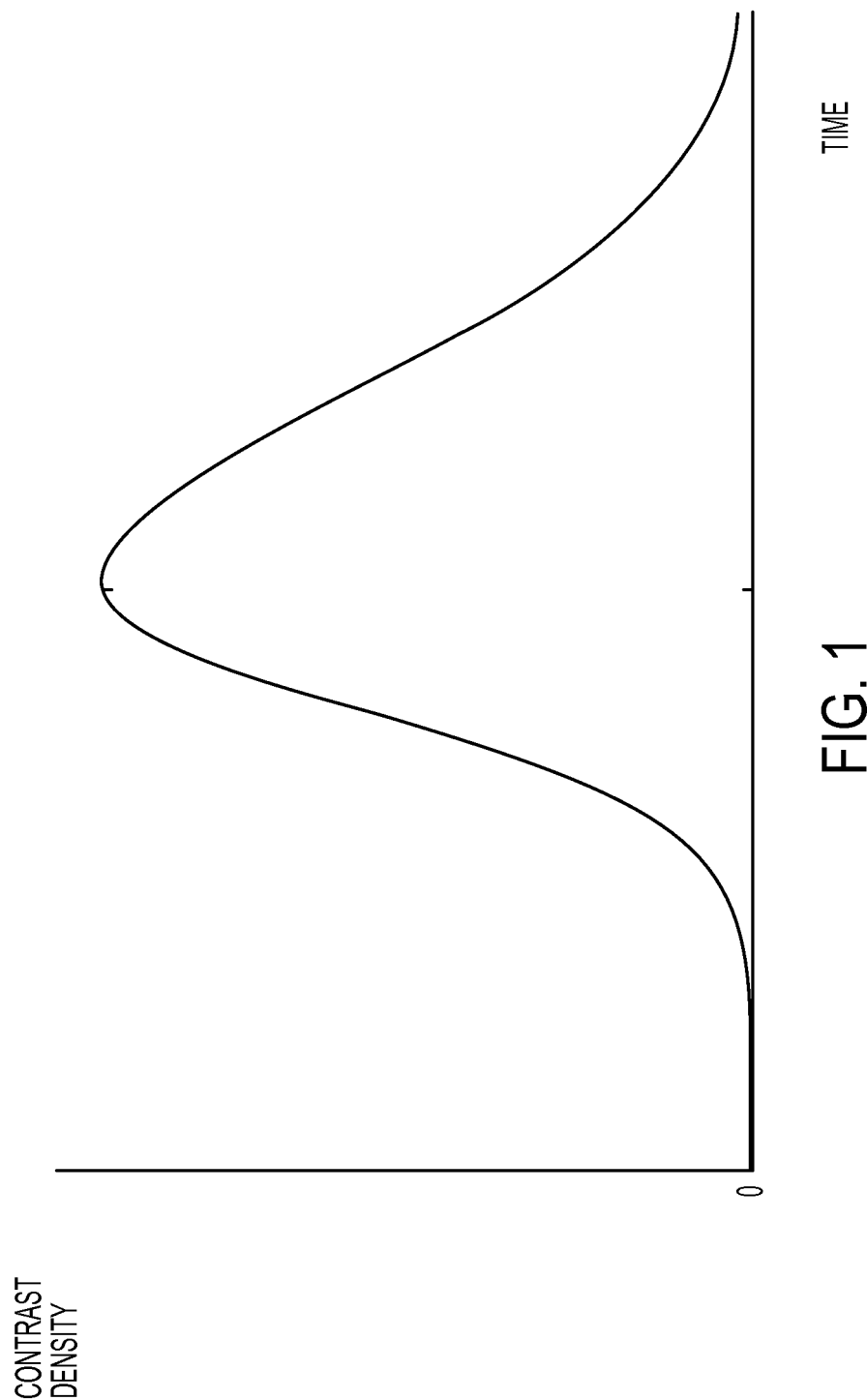
FIG. 1 is a typical time-contrast curve obtained or generated from a DSA image sequence.
Figure 2:
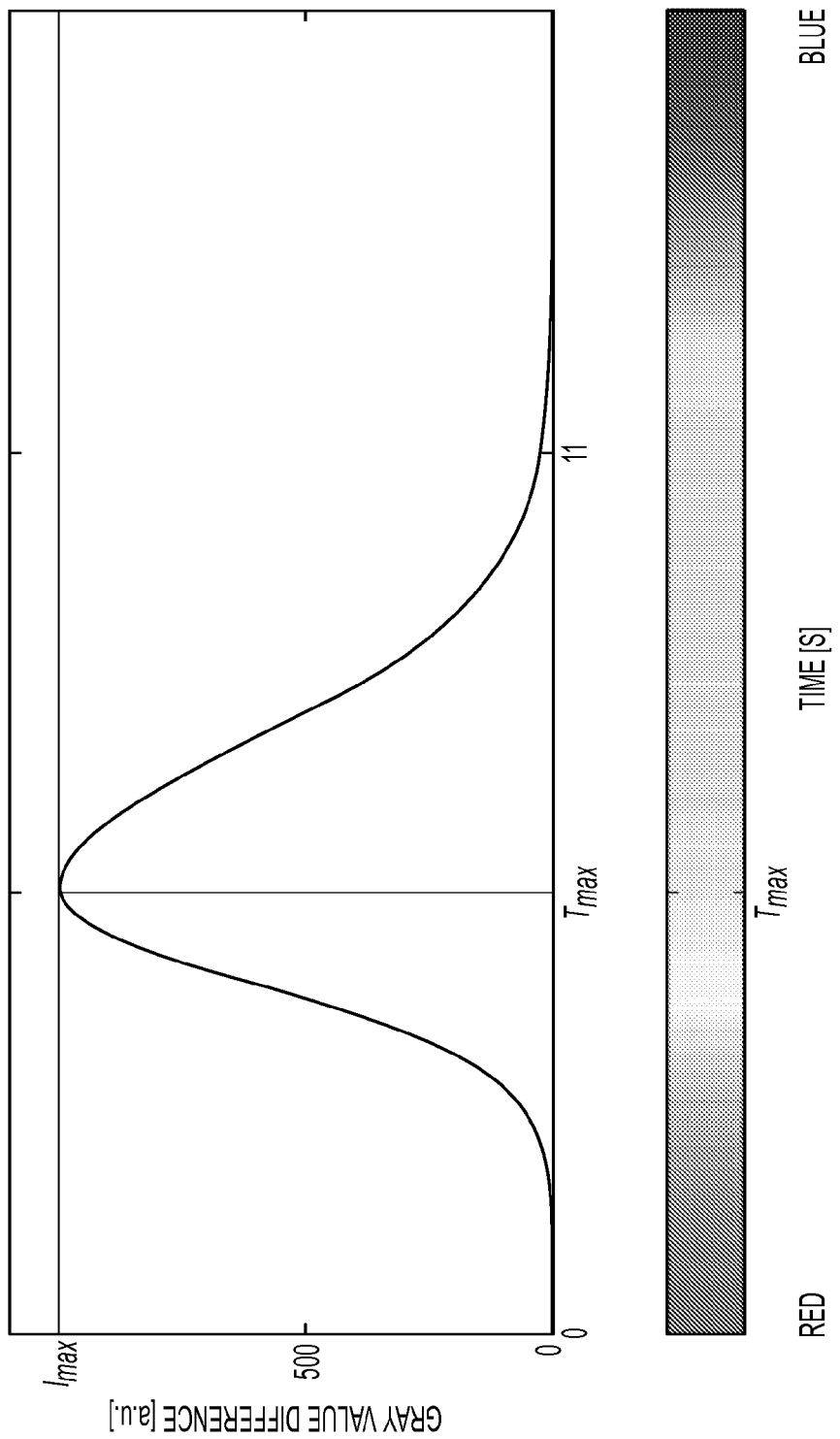
FIG. 2 illustrates an existing method of visualizing DSA data with reference to a time-contrast curve.
Figure 3:
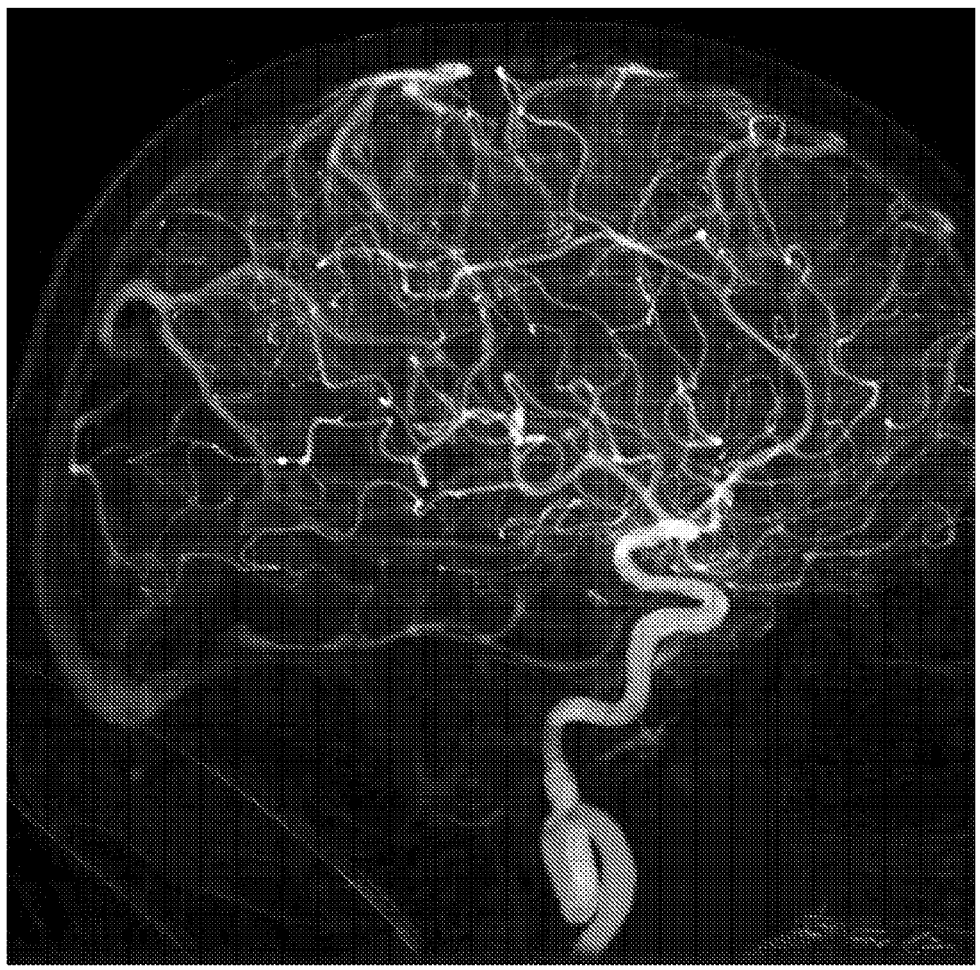
FIG. 3 is an image resulting from the application of the existing method of FIG. 2.
Figure 4:
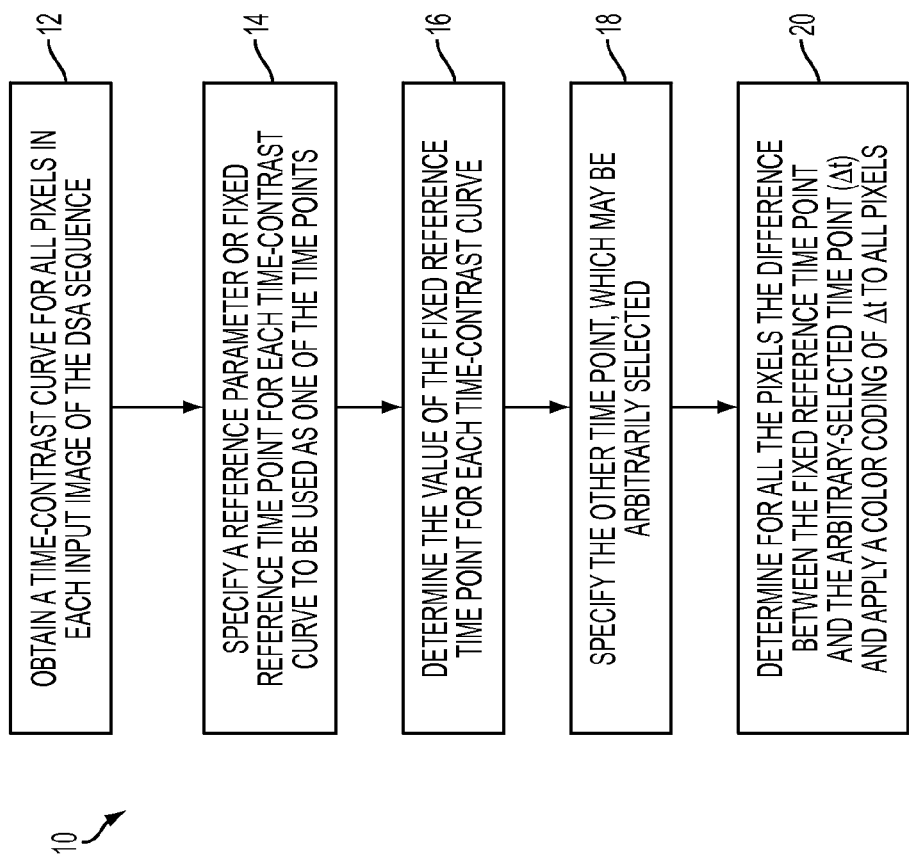
FIG. 4 is a flowchart of an embodiment of a method carried out in accordance with the present invention.

FIG. 4 is a simplified flowchart of an embodiment of a method 10 carried out in accordance with the present invention. Generally, the method 10 carries out color-coding the amount of time passed between two time points ($\Delta T$) as opposed to color coding distinct time points of the time-contrast curve. This means the method 10 color codes time differences instead of time points. Furthermore, since the time points can be specified arbitrarily, the method 10 allows the production of an animated representation of the angiographic data.

More specifically, the user acquires a DSA image sequence of a respective region of interest of the patient. The method 10 generates or calculates a time-contrast curve for all pixels in each input image/frame of the DSA sequence (Step 12). The user also specifies a reference parameter or fixed reference time point $T_{ref}$ for each time-contrast curve (Step 14) to be used as one of the time points for the method 10. This may be, for example, the "time-to-peak opacification" $T_{max}$ as described above or any other pixel-specific temporal parameter determined from the input DSA data. The value of the fixed reference time point $T_{ref}$ is determined for each time-contrast curve obtained from the DSA image sequence (Step 16).

Figure 5:
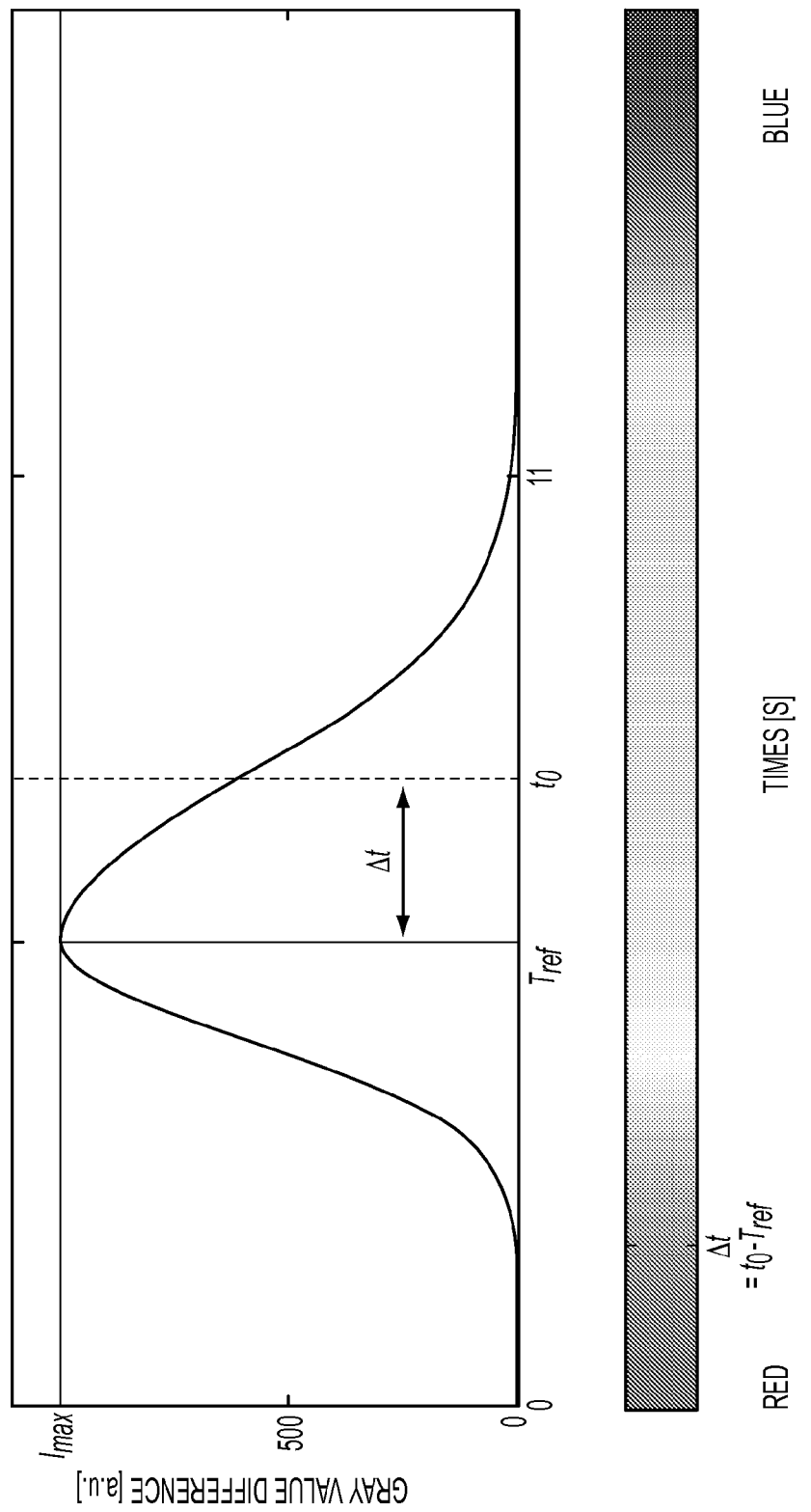
FIG. 5 illustrates the method of FIG. 4 with reference to a time-contrast curve.
Figure 6:
FIG. 6 is an exemplary image resulting from the application of the method of FIG. 4.

The other time point, $t_0$ can be specified or chosen arbitrarily by the user (permitting the aforementioned animation capability) (Step 18). This other time point $t_0$ is a global time parameter, i.e. not pixel-specific. The method 10 determines for all the pixels the difference between the fixed reference time point $T_{ref}$ and the arbitrarily-selected time point $t_0$ and applies a color coding of $\Delta t = t_0 - T_{ref}$ to all pixels of the input data (Step 20). Any color coding technique may be applied. This results in an image that encodes the pixel-specific information "amount of time passed between $T_{ref}$ and $t_0$". FIG. 5 shows an example of temporal difference encoding for one pixel with reference to a time-contrast curve with $T_{ref} = T_{max}$ and an arbitrary image-global time point $t_0$, with an arbitrary color mapping (the figure shows a red through blue spectrum bar along the time axis, the marked $\Delta t$ being within the light green to green scale). FIG. 6 shows an example rendering of a resulting temporal difference encoding image. In FIG. 6, the brightest blood vessels (the larger vessels mainly in the image center, from bottom to middle, and at the bottom right side of the image) are color-coded in green or light green. Fainter blood vessels (the smaller vessels throughout the right side of the image) are mainly greenish; some vessels in the middle of the right side are reddish.

Note that the amount of time passed between two time points can be a positive or negative number. This reads as "amount of time at $t_0$ passed since $T_{ref}$" and "amount of time at $t_0$ until reaching $T_{ref}$", respectively. This means that it is possible to color code positive as well as negative difference values using the method 10.

Figure 7:
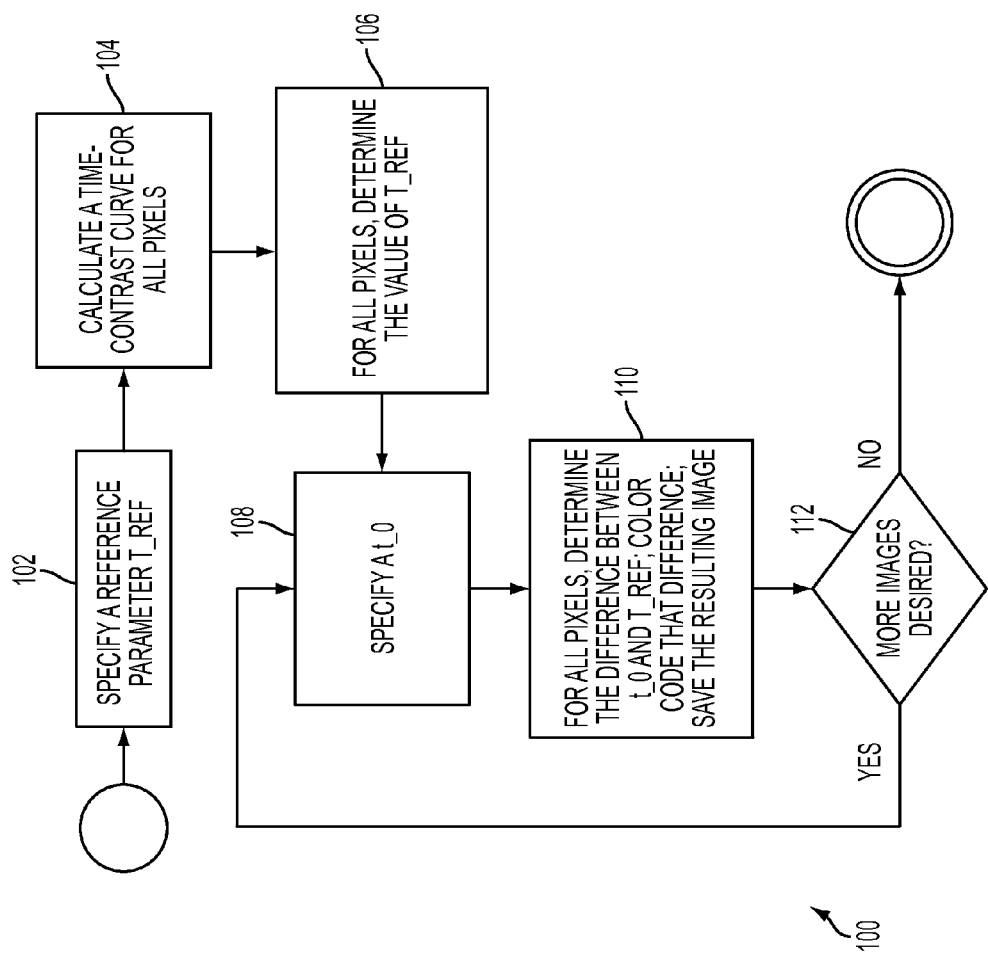
FIG. 7 is a schematic of a second embodiment of a method carried out in accordance with the present invention.

FIG. 7 is a schematic of a second embodiment of a method 100 carried out in accordance with the present invention. Regardless of the specified fixed reference time point $T_{ref}$ and the chosen color coding technique (described in more detail below), the method 100 produces an animated representation of the temporal phenomena in angiographic data. This animated representation can be generated off-line or on the fly (during the imaging operation), allowing the user to interact with the DSA sequence by specifying the temporal parameters interactively.

More specifically, the user acquires a DSA image sequence of a respective region of interest of the patient. The user also specifies a reference parameter or fixed reference time point $T_{ref}$ for each time-contrast curve (Step 102) to be used as one of the time points. This may be, for example, the "time-to-peak opacification" $T_{max}$ as described above or any other pixel-specific temporal parameter determined from the input DSA data. The method 100 generates or calculates a time-contrast curve for all pixels in each image of the DSA sequence (Step 104). The value of the fixed reference time point $T_{ref}$ is determined for each time-contrast curve obtained from the DSA image sequence (Step 106).

Figure 8:
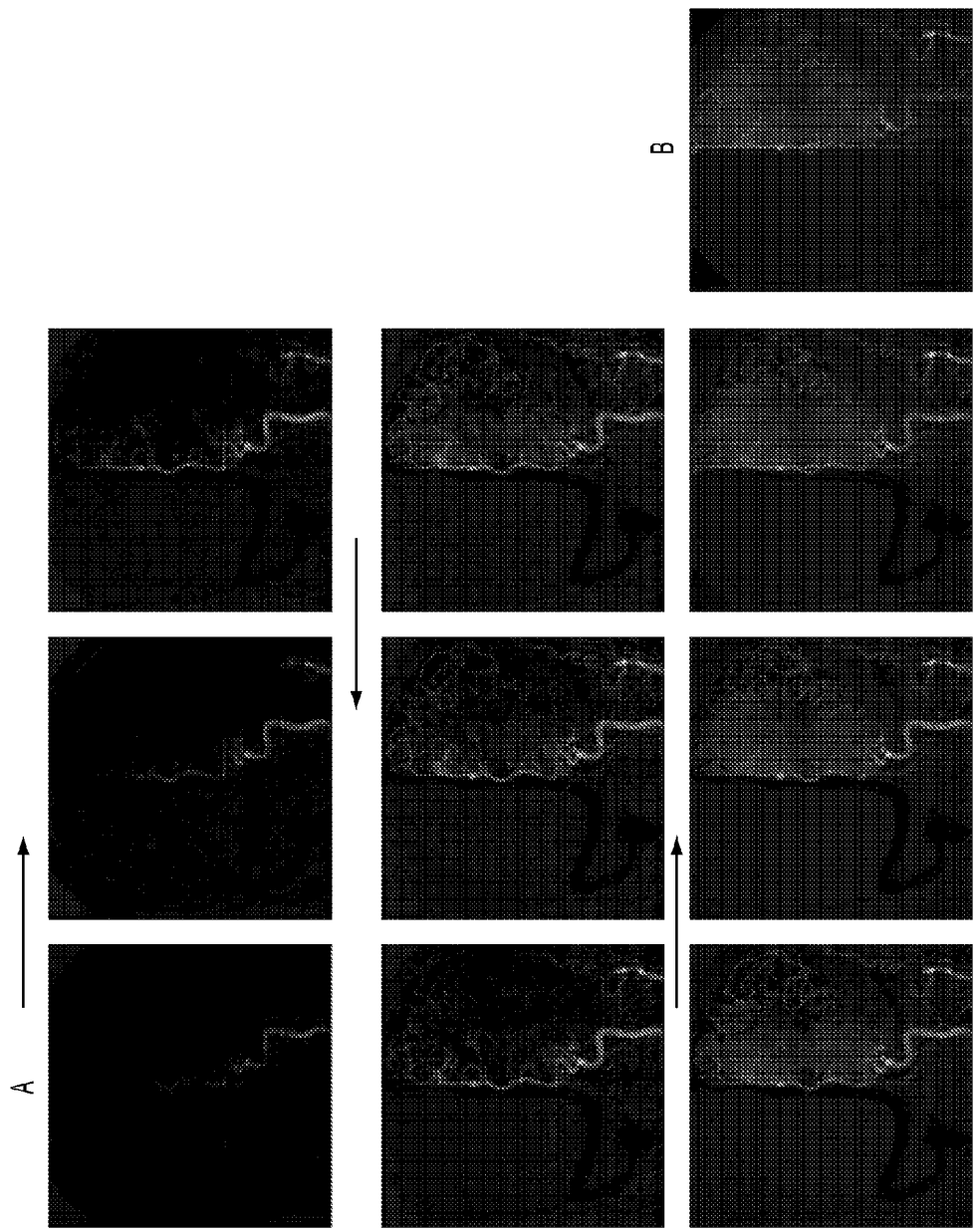
FIG. 8 is an exemplary image sequence resulting from the application of the method of FIG. 7.

The other time point, $t_0$ can be specified or chosen arbitrarily by the user (permitting the aforementioned animation capability) (Step 108). This other time point $t_0$ is a global time parameter, i.e. not pixel-specific. The method 100 determines for all the pixels the difference between the fixed reference time point $T_{ref}$ and the arbitrarily-selected time point $t_0$ and applies a color coding of $\Delta t = t_0 - T_{ref}$ to all pixels of the input data (Step 110). Any color coding technique may be applied. This produces an output image that encodes the pixel-specific information "amount of time passed between $T_{ref}$ and $t_0$". If more images are desired, the user may increment or decrement the arbitrarily-selected time point $t_0$ by a fixed or variable amount and repeat the remainder of the method 100. FIG. 8 shows an example rendering of a sequence of resulting temporal difference encoding images with the arbitrarily-selected time point $t_0$ increasing in 10% steps from start (image A) to end (image B) (solid arrows indicating the progression). This sequence may then be displayed as an animation. In FIG. 8, the first two images show a few bright, large blood vessels in the image center, from bottom to middle, that are reddish. The next four images show large and small blood vessels, the brightest are in the image center, from bottom to middle and at the bottom right; the color coding of these vessels progresses from yellow/red to green. In the last four images, fainter smaller blood vessels may be seen throughout the right side of the images in a greenish color; the brightest vessels are in the image center, from bottom to middle and at the bottom right and their color coding progresses from green-blue through blue-green to dark blue. In the last image (image B), some dull reddish-colored blood vessels on the left side of the image may also be seen.

As noted above, neither method 10, 100 of the invention is limited to any particular type of color encoding technique or look-up. Instead, the two methods 10, 100 are directed to color-coding time differences in DSA series and, in the second embodiment, to vary one of the parameters such that an animated representation of the respective temporal contrast agent flow information results. In both methods 10, 100, the other parameter is a pixel-specific property of the time-contrast curve. The following examples serve to illustrate color-coding for $T_{ref} = T_{max}$:

a. "flow-in" visualization:

$$\text{pixel color} = \begin{cases} \text{color lookup,} & \text{if } t_0 < t_{ref} \\ \text{black,} & \text{otherwise;} \end{cases}$$

b. "flow-out" visualization:

$$\text{pixel color} = \begin{cases} \text{black,} & \text{if } t_0 < t_{ref} \\ \text{color lookup,} & \text{otherwise;} \end{cases}$$

c. alternative "flow-in" visualization $$\text{pixel color} = \begin{cases} \text{color lookup,} & \text{if } t_0 < t_{ref} \\ \text{original image,} & \text{otherwise;} \end{cases}$$

d. alternative "flow-out" visualization $$\text{pixel color} = \begin{cases} \text{original image,} & \text{if } t_0 < t_{ref} \\ \text{color lookup,} & \text{otherwise;} \end{cases}$$

and e. encode "time-since" (i.e., positive amount of time) and "time-until" (i.e., negative amount of time) information differently by using different color ranges for $t_0 < t_{ref}$ and $t_0 > t_{ref}$.

Figure 9:
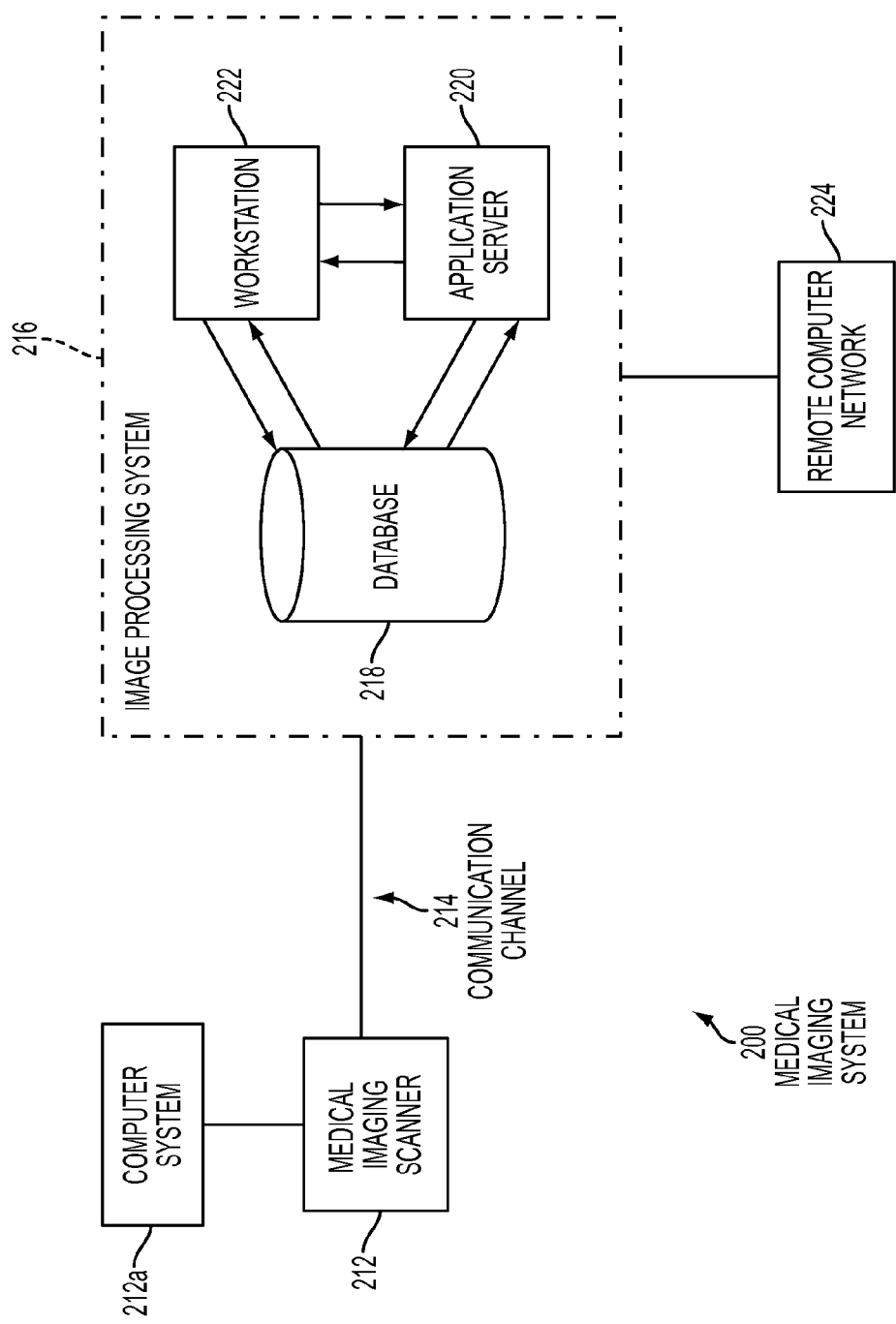
FIG. 9 is a block diagram of a medical imaging system (simplified) that may implement the embodiments of a method carried out in accordance with the present invention.

FIG. 9 is a block diagram of a medical imaging system 200 (simplified) that may implement the methods 10, 100. The system 200 comprises a medical imaging scanner 212 that acquires image data of a patient under examination, for example, a region of the vasculature of the patent. As noted above, the scanner 212 may use X-ray imaging (e.g. using fluoroscopy) or other appropriate imaging modality to acquire the image data such as fluoroscopy sequences, 3D datasets (C-arm CT imaging), and 2D DSA sequences. The scanner 212 may acquire raw image data from multiple scanned views of the region of interest of the patient, record or reconstruct the images, and produce image data signals for the multiple views. This may be done in real-time or near real-time. The image data signals may be in Digital Imaging and Communications in Medicine (DICOM) format. Other formats may also be used.

The imaging scanner 212 is operably connected to a computer system 212a that controls the operation of the scanner 212 and, via a communication channel 214, to an image processing system 216 that processes the image data signals utilizing appropriate image processing software applications. The image processing system 216 has an image data archive or database 218, an application server 220, and a user workstation 222. The components of the image processing system 216 are interconnected via a communications network that may be implemented by physical connections, wireless communications, or a combination. The image data archive or database 218 is adapted to store the image data signals that are produced by the image scanner 212 as well as the results of any additional operations on the image data signals by the other components of the image processing system 216. The image data archive or database 218 is also adapted to store pre-acquired imaging data (obtained via any appropriate imaging modality) or models of the anatomy or region of interest. The image data archive or database 218 may be a Picture Archiving and Communications System (PACS). Other types of image data archives or databases may also be used.

The user workstation 222 is adapted to control the operation of the imaging processing system 216 and its various components. The user workstation 222 particularly operates the application server 220 and the various image processing software applications that are stored in, or are accessible by, the server 220. The application server 220 also manages and coordinates the image data sets among the image processing applications. The image processing applications may include, for example, visualization applications, computer-aided diagnosis (CAD) applications, medical image rendering applications, anatomical segmentation applications, image registration applications, or any other type of medical image processing application. The image processing applications may also include the methods 10, 100 and those of the respective various steps. The image data archive or database 218, applications server 220, and the user workstation 222 may also each be connected to a remote computer network 224 for communication purposes or to access additional data or functionality. The workstation 222 may comprise appropriate user interfaces, like displays, storage media, input/output devices, etc.

The various components of the imaging system 200 are conventional and well known components. They may be configured and interconnected in various ways as necessary or as desired. The imaging system 200 and, in particular, the image processing system 216 is adapted to permit the imaging system 200 to operate and to implement methods in accordance with embodiments of the invention, for example, as shown in FIGS. 4 and 7.

The invention provides novel methods for visualizing temporal data for DSA and other angiographic data. Rather than color-encoding absolute time points, time differences are encoded. This allows for a per-pixel encoding of information relative to a reference time point. Exemplary types of information are "time passed since bolus (contrast agent) arrival", "time until end of wash out", and many more. The invention also allows for animated renderings of the data by dynamically changing the reference time point. Advantageously, the invention can lead to new clinical software solutions whose application may improve the quality of the diagnosis, the assessment, as well as the interventional treatment of patients, e.g., those suffering from cerebral vascular disorders such as tumors, strokes, and AVMs (arteriovenous malformations).

Other modifications are possible within the scope of the invention. For example, the subject patient to be scanned may be a human subject, animal subject or any other suitable object. Also, any combination of one or more color coding techniques may be used to visualize any relation between any of the temporal parameters described above, in order to create one or more output images. Also, the present invention may be used for other medical interventional applications having a need for visualizing DSA data, besides intravascular therapies, as well as for non-medical applications.

Also, although the steps of the methods 10, 100 have been described in a specific sequence, the order of the steps may be re-ordered in part or in whole and the steps may be modified, supplemented, or omitted as appropriate. Also, the methods 10, 100 may use various well known algorithms and software applications to implement the steps and substeps. Further, the methods 10, 100 may be implemented in a variety of algorithms and software applications. Further, the methods 10, 100 may be supplemented by additional steps or techniques. It is also understood that the methods 10, 100 may carry out all or any of the steps using real-time data, stored data from a data archive or database, data from a remote computer network, or a mix of data sources.

Also, the various described instrumentation and tools may be configured and interconnected in various ways as necessary or as desired. Further, although in the described methods 10, 100 the user may use self-contained instrumentation and tools, the user may use other instrumentation or tools in combination with or in place of the instrumentation and tools described for any step or all the steps of the methods 10, 100, including those that may be made available via telecommunication means. Further, the described methods 10, 100, or any steps, may be carried out automatically by appropriate instrumentation and tools or with some manual intervention.

What is claimed is:

1. A method of visualizing changes in blood flow in a digital subtraction angiography (DSA) image sequence, comprising:
   a. generating a time-contrast curve for all pixels in each image of the DSA image sequence;

b. specifying a reference parameter for each time-contrast curve to be used as a first time point;
c. determining the value of the reference parameter for each time-contrast curve;
d. specifying an arbitrary parameter for each time-contrast curve to be used as a second time point; and
e. producing an output image by applying a color-coding of the difference between the first time point and the second time point to all pixels.

2. The method of claim 1, wherein the reference parameter comprises a fixed reference time point.

3. The method of claim 2, wherein the fixed reference time point comprises a pixel-specific temporal parameter determined from the DSA image sequence.

4. The method of claim 2, wherein the fixed reference time point comprises a time-to-peak opacification time point.

5. The method of claim 1, wherein the arbitrary parameter comprises a global time parameter that is not pixel-specific.

6. The method of claim 1, wherein the difference between the first time point and the second time may be a positive value or a negative value.

7. The method of claim 1, further comprising:
producing at least one additional output image by changing the value of the arbitrary parameter by a fixed or variable amount;
applying a color-coding of the difference between the first time point and the changed second time point to all pixels; and
producing a dynamic series of output images.

8. The method of claim 1, further comprising producing an animation of output images by repeating the specifying an arbitrary parameter and producing steps to obtain a plurality of output images for dynamic display.

9. A method of visualizing temporal data for digital subtraction angiography (DSA) and other angiographic data of an image, comprising: obtaining a time-contrast curve for all pixels in the image; specifying a first time point and a second time point for each time-contrast curve; and producing an output image that encodes the time differences between the first and second time points.

10. The method of claim 9, wherein one of the first and second time points comprises a fixed reference time point.

11. The method of claim 10, wherein the first fixed reference time point comprises a pixel-specific parameter of the time-contrast curve.

12. The method of claim 9, wherein one of the first and second time points comprises an arbitrarily-selected time point.

13. The method of claim 12, wherein the arbitrarily-selected time point comprises a global non-pixel-specific parameter of the time-contrast curve.

14. The method of claim 9, wherein producing comprises producing an output image that color-encodes the time differences between the first and second time points in the image.

15. The method of claim 9, wherein the time differences have either positive difference values or negative difference values.

16. The method of claim 9, further comprising dynamically changing one of the first and second time points such that an animated representation of the DSA and other angiographic data of the image results.

17. The method of claim 9, further comprising varying one of the first and second time points to obtain a sequence of temporal difference encoding images and producing a dynamic image sequence.

18. A system for visualizing temporal data for angiographic images, comprising an imager that acquires image data of an anatomical region of a patient and a processor that manipulates the image data to produce a single image which is color-encoded for the time difference between two selected time points of a time-contrast curve for each respective pixel of the image data.

19. The system of claim 18, wherein said processor manipulates the image data to produce a dynamic series of images, each of which is color-encoded for the time difference between two respective selected time points of a time-contrast curve for each respective pixel of the image data.

* * * * *